US010926018B2

(12) United States Patent
Hobro et al.

(10) Patent No.: US 10,926,018 B2
(45) Date of Patent: Feb. 23, 2021

(54) RENAL FAILURE THERAPY SYSTEM AND METHOD FOR ELECTRICALLY SAFE TREATMENT

(71) Applicant: GAMBRO LUNDIA AB, Lund (SE)

(72) Inventors: Sture Hobro, Lund (SE); Erik Torgny, Lund (SE)

(73) Assignee: Gambro Lundia AB, Lund (SE)

( * ) Notice: Subject to any disclaimer, the term of this patent is extended or adjusted under 35 U.S.C. 154(b) by 324 days.

(21) Appl. No.: 15/766,185

(22) PCT Filed: Oct. 14, 2016

(86) PCT No.: PCT/EP2016/074710
§ 371 (c)(1),
(2) Date: Apr. 5, 2018

(87) PCT Pub. No.: WO2017/064251
PCT Pub. Date: Apr. 20, 2017

(65) Prior Publication Data
US 2018/0289881 A1    Oct. 11, 2018

(30) Foreign Application Priority Data
Oct. 14, 2015  (SE) .................................. 1551325-2

(51) Int. Cl.
*A61M 1/34* (2006.01)
*A61M 1/16* (2006.01)
*A61M 1/36* (2006.01)
(52) U.S. Cl.
CPC ............ *A61M 1/3413* (2013.01); *A61M 1/16* (2013.01); *A61M 1/1621* (2014.02); *A61M 1/34* (2013.01);
(Continued)

(58) Field of Classification Search
CPC .... A61M 1/3413; A61M 1/34; A61M 1/3621; A61M 1/16; A61M 1/3624;
(Continued)

(56) References Cited

U.S. PATENT DOCUMENTS 3,808,502 A  4/1974 Babilus
4,155,852 A  5/1979 Fischel et al.
(Continued)

FOREIGN PATENT DOCUMENTS

BR  PI1105132-9 A2  11/2013
CN  102341796 A  2/2012
(Continued)

OTHER PUBLICATIONS

Notice of Opposition filed by Fresenius Medical Care AC & Co. KGaA in related EP Patent Application No. 2616117B1 on Sep. 9, 2016.
(Continued)

*Primary Examiner* — Liam Royce
(74) *Attorney, Agent, or Firm* — K&L Gates LLP

(57) ABSTRACT

A renal failure therapy system (10) includes a dialyzer (102); a blood circuit (100) in fluid communication with the dialyzer (102); a dialysis fluid circuit (30) in fluid communication with the dialyzer (102); a housing supporting the dialyzer (102), the blood circuit (100) and the dialysis fluid circuit (30); and at least one electrical socket (170) held by the housing, the electrical socket (170) providing a voltage output dedicated to a particular voltage type of external electrical device (200) for powering or charging the external electrical device (200), the at least one electrical socket (170) including electrical insulation for protecting a patient while powering the external electrical device (200).

19 Claims, 7 Drawing Sheets

(52) U.S. Cl.
CPC .......... *A61M 1/367* (2013.01); *A61M 1/3621* (2013.01); *A61M 1/3624* (2013.01); A61M 2205/3331 (2013.01); A61M 2205/3351 (2013.01); A61M 2205/3368 (2013.01); A61M 2205/502 (2013.01)

(58) Field of Classification Search
CPC ................ A61M 1/1621; A61M 1/367; A61M 2205/3351; A61M 2205/502; A61M 2205/3368; A61M 2205/3331
See application file for complete search history.

(56) References Cited

U.S. PATENT DOCUMENTS

| | | | |
|---|---|---|---|
| 4,443,333 | A | 4/1984 | Mahurkar |
| 5,174,293 | A | 12/1992 | Hagiwara |
| 5,578,223 | A | 11/1996 | Bene et al. |
| 5,736,038 | A | 4/1998 | Stoughton |
| 5,807,253 | A | 9/1998 | Dumoulin et al. |
| 6,136,201 | A | 10/2000 | Shah et al. |
| 8,180,443 | B1 | 5/2012 | Kleinekofort et al. |
| 2003/0195453 | A1 | 10/2003 | Han et al. |
| 2003/0209475 | A1 | 11/2003 | Connell et al. |
| 2003/0217961 | A1* | 11/2003 | Hopping ............... A61M 1/288 210/258 |
| 2003/0218623 | A1 | 11/2003 | Krensky et al. |
| 2003/0220598 | A1 | 11/2003 | Busby et al. |
| 2004/0006319 | A1* | 1/2004 | Lina .................... A61M 1/0031 604/304 |
| 2004/0019312 | A1 | 1/2004 | Childers et al. |
| 2004/0113498 | A1* | 6/2004 | Kroenke ............... A61B 5/0017 307/115 |
| 2004/0267183 | A1 | 12/2004 | Chevallet |
| 2005/0045540 | A1 | 3/2005 | Connell et al. |
| 2005/0131332 | A1 | 6/2005 | Kelly et al. |
| 2006/0177351 | A1 | 8/2006 | Heiniger et al. |
| 2008/0065006 | A1 | 3/2008 | Roger et al. |
| 2008/0145249 | A1* | 6/2008 | Smisson ................ A61M 5/44 417/474 |
| 2009/0046402 | A1 | 2/2009 | Malkus et al. |
| 2009/0177149 | A1 | 7/2009 | Childers et al. |
| 2010/0022935 | A1 | 1/2010 | Muller |
| 2010/0168653 | A1 | 7/2010 | Levin |
| 2010/0312161 | A1 | 12/2010 | Jonsson et al. |
| 2012/0185619 | A1 | 7/2012 | Levin |
| 2013/0158469 | A1 | 6/2013 | Hopping et al. |
| 2014/0290151 | A1* | 10/2014 | Lee ........................... E04B 2/74 52/32 |

FOREIGN PATENT DOCUMENTS

| | | |
|---|---|---|
| CN | 104380296 A | 3/2012 |
| CN | 203445788 U | 2/2014 |
| CN | 104080513 A | 10/2014 |
| CN | 104203334 A | 12/2014 |
| DE | 3512533 | 10/1986 |
| EP | 0458041 | 11/1991 |
| EP | 0611228 | 8/1994 |
| EP | 0820776 | 1/1998 |
| GB | 927349 | 5/1963 |
| JP | 1024102 | 1/1998 |
| JP | 1085323 | 4/1998 |
| WO | 9306875 | 4/1993 |
| WO | 9411093 | 5/1994 |
| WO | 2005044339 | 5/2005 |
| WO | 2008031539 | 3/2008 |
| WO | 2009044220 | 4/2009 |
| WO | 2009090382 | 7/2009 |
| WO | 2010011441 | 1/2010 |
| WO | 2010077762 | 7/2010 |

OTHER PUBLICATIONS

Eidesstattliche Versicherung von Herrn Dr. Jorg Dreyhsig. Affidavit of Dr. Jorg Dreyhsig asserting the booklet referred to as D13 (Fresenius Medical Care: Prospekt: Acute Therapy Systems: multiFiltrate, 2006) was available to the public at the ERA-EDTA conference in Glasgow, UK in 2006. D13.

DIN EN 60601-1 (VDE 0750-1), Seiten 84-87 (Jul. 2007). Medical electrical equipment—Part 1 : General requirements for basic safety and essential performance (IEC 60601-1 :2005); German version EN 60601-1:2006. D16.

C. Ronco et al., "Critical Care Nephrology," Kluwer Academic Publishers, 1998. 7 pages. D12.

ANSIIAAMI ES1-1993. American National Standard. Current safe limits for electromedical apparatus. Developed by Association for the Advancement of Medical Instrumentation. Dec. 2, 1993. D15.

Jonsson et al., "Blood lines conduct leakage current during haemodialysis: a potential safety risk during first failure, especially for patients with central dialysis catheter as access", Med. Bioi. Eng. Comput., 2005, 43, 731-738, 8 total pages.

Non-Final Office Action issued in U.S. Appl. No. 13/824,892 dated Jul. 14, 2016.

Final Office Action issued in U.S. Appl. No. 13/824,892 dated Jan. 25, 2017.

Non-Final Office Action issued in U.S. Appl. No. 13/824,892 dated Jul. 11, 2017.

Response to the Non-Final Office Action dated Jul. 11, 2017 in U.S. Appl. No. 13/824,892. Response dated Nov. 8, 2017.

Final Office Action issued in U.S. Appl. No. 13/824,892 dated Feb. 22, 2018.

International-Type Search Report issued in related Swedish Patent Application No. SE1551325-2 dated May 4, 2016.

Office Action issued in related Swedish Patent Application No. SE1551325-2 dated May 4, 2016.

International Search Report issued in International Patent Application No. PCT/EP2016/074710 dated Jan. 3, 2017.

Written Opinion issued in International Patent Application No. PCT/EP2016/074710 dated Jan. 3, 2017.

Chinese First Office Action issued in related Chinese Patent Application No. 2016800604329 dated Mar. 19, 2010—19 Pages.

Chinese Search Report issued in related Chinese Patent Application No. 2016800604329 dated Mar. 9, 2020—3 Pages.

* cited by examiner

RENAL FAILURE THERAPY SYSTEM AND METHOD FOR ELECTRICALLY SAFE TREATMENT

PRIORITY CLAIM

The present application is a National Phase of International Application No. PCT/EP2016/074710, filed on Oct. 14, 2016, which claims priority to Swedish Patent Application No. 1551325-2, filed on Oct. 14, 2015, the entire contents of each of which are being incorporated herein by reference.

BACKGROUND

The present disclosure relates generally to medical systems. More specifically, the present disclosure relates to medical systems that allow a patient to safely power an external electronic device during treatment.

Hemodialysis ("HD") in general uses diffusion to remove waste products from a patient's blood. A diffusive gradient that occurs across the semi-permeable dialyzer between the blood and an electrolyte solution called dialysis fluid causes diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism, which is particularly beneficial in removing middle and large molecules (in hemodialysis there is a small amount of waste removed along with the fluid gained between dialysis sessions, however, the solute drag from the removal of that ultrafiltrate is typically not enough to provide convective clearance).

Hemodiafiltration ("HDF") is a treatment modality that combines convective and diffusive clearances. HDF flows dialysis fluid through a dialyzer, similar to standard hemodialysis, providing diffusive clearance. In addition, substitution solution is provided directly to the extracorporeal circuit, providing convective clearance. These modalities are administered by a dialysis machine. The machines may be provided in a center or in a patient's home. Dialysis machines provided in a center are used multiple times a day for multiple patients and therefore must be cleaned between treatments. Dialysis machines use multiple components, including electrical components.

Outside electrical devices have the potential to expose people to the risk of spurious electric currents. In the case of medical electrical equipment (and dialysis machines in particular), the risk is potentially greater how depending upon the equipment is connected to the patient. Patients connected to present dialysis machines may be poorly safeguarded against leakage current due to contact with external electrical equipment, such as bed lamps, electrically adjustable beds or treatment chairs, lap tops, phones connected to chargers, and other electrical equipment that is in turn connected to a mains electrical power source. Poor quality chargers are especially dangerous as their electrical insulation may break down, leading to fault currents that may run to the patient. It is accordingly advisable for dialysis clinics to ask that patients during treatment not plug their electronic devices into an external power source, which may be inconvenient for patients undergoing a treatment that may last for hours.

It is accordingly desirable to provide a system that allows a patient to use and power an external electronic device during treatment safely.

SUMMARY

The present disclosure provides a renal failure therapy system and method that performs hemodialysis ("HD"), hemofiltration ("HF") and hemodiafiltration ("HDF"). Accordingly, "renal failure therapy" as used herein is meant to include any one, or more, or all of HD, HF and/or HDF.

The renal failure therapy system and method of the present disclosure includes a machine providing at least one electrically insulated electrical socket, which enables a patient undergoing treatment to power an external device, such as a smartphone, personal computer, reading lamp and the like. The goal of the electrical insulation is to provide an extra galvanic separation between the patient and the machine to minimize leakage or fault currents. For AC current sockets, the electrical insulation may include a transformer that provides galvanic isolation forming an open circuit, which prevents propagation of fault currents. The transformer has an input coil separated physically from an output coil. The input coil magnetically induces a desired AC voltage in the output coil. The desired AC output voltage charges or powers the user's electrical device, such as a computer.

For DC sockets, the electrical insulation may take multiple forms. One form of DC insulation uses DC to AC conversion. The DC input voltage is converted to an AC input voltage, which then powers an input coil. The AC input coil magnetically induces an AC output voltage in an output coil as described above. Here, however, the AC output voltage is converted into a desired DC voltage, typically 5 VDC, 12 VDC or 24 VDC, for powering and/or charging the user's electrical device. Other DC insulation providing galvanic protection for low voltages may include optical means.

The machine may have multiple electrically insulated sockets, for example, providing an array of desirable output voltages of 5 VDC, 12 VDC, 24 VDC, 120 VAC, and/or 220 VAC. It is contemplated to provide banks of electrically insulated sockets of the same output voltage, for example, a bank of sockets providing output voltages of 5 VDC. Where coiled transformers are used, the banks may have a single primary coil for multiple secondary coils, or a single primary coil for each secondary coil.

The electrically insulated electrical sockets may be located on the front of the renal failure therapy machine, or at another location on the machine that is readily accessible to the patient and/or nurse. It is ensured that the electrically insulated electrical sockets are well made, so that they provide robust electrical insulation. Indeed, the sockets may provide two layers of electrical insulation (or double insulation). In this manner, it is assured that the patient may safely plug his or her electrical device into the renal failure therapy machine during treatment for operation and/or charging.

As discussed, the electrically insulated sockets allow the user to safely power their external electrical devices during treatment. To make treatment even safer, it is contemplated to combine the electrically insulated sockets with other electrical insulation, which protects the patient electrically towards a fluid path in the renal failure therapy machine. That is, one may think of the patient as being placed electrically between the external electrical device connected to the clinic's mains power system and electrical earth via a path that runs through the blood lines, the patient, the conductive dialysis fluid lines in the machine, and outside the machine through an external used dialysate drain line. The electrically insulated sockets place a layer (or double layer) of electrical protection between the patient and the clinic's mains power system. It is also contemplated to place a layer of electrical protection between the patient and electrical earth via the conductive fluidic pathway through the renal failure therapy machine.

In one embodiment, the layer of electrical protection between the patient and electrical earth includes an electrically floating fluid pathway. Generally, an electrically floating fluid pathway is one that is not connected to electrical earth. As used herein, electrically floating fluid pathway in one embodiment means instead that there is no pathway to electrical earth within the blood lines, dialysis fluid lines either inside the machine or outside the machine towards the dialyzer, concentrate lines, or even the water lines (e.g., if the water is non-deionized). That is, electrically floating fluid pathway may mean a fluid pathway which, when carrying an electrically conductive fluid therein, would itself render the conductive fluid electrically floating relative to an electrical potential, such as electrical earth, provided to the dialysis machine through the mains and/or through earthed parts connected to the dialysis machine (e.g. drain and external water lines). The electrically floating fluid pathway may include the entire or one or several portion(s) of the blood lines, (fresh and/or used) dialysis fluid lines, concentrate lines, and/or water lines as well as components, such as sensors and pumps, connected to the above mention fluid lines. The only pathway to electrical earth is via the used dialysis fluid traveling outside the machine through an external drain line to electrical earth, for example, at the clinic's house drain. Making any fault voltages generated at the patient travel all the way to electrical earth at the house drain increases the naturally occurring impedances within the fluid lines that the fault voltage sees, thereby minimizing the current generated by the fault voltage.

There are a number of structural modifications made to allow the machine to operate with an electrically floating fluid pathway. First, dialysis machines typically intentionally connect various flow components to protective earth. For example, sensing equipment is typically connected to a signal ground to divert fault currents away from the sensing equipment to prevent false readings. The signal ground may be connected to protected earth in the dialysis machine directly or indirectly via the dialysis fluid. The electrically floating pathway of the present disclosure cannot exist with such connections to protective earth. Instead, the sensitive equipment is here provided with electrical bypassing, which bypasses fault currents around the equipment, through the electrically floating fluid pathway and through an external used dialysate drain line, to electrical earth at the house drain.

Second, certain flow components, such as the sensing equipment, have probes or other conductive structures that contact the medical fluid, such as dialysis fluid. Any such component becomes a potential pathway to electrical earth due to its wiring. In the present disclosure, the wiring of any such component is electrically isolated with a single or double layer of electrical insulation in the same manner as the electrically insulated electrical sockets discussed herein.

The above-described combination of electrical insulation prevents or reduces fault voltages generated due to the powering of a patient's external personal electrical equipment (a notoriously large source of fault voltages) from occurring. The combination also forces any fault voltages that don't occur at the patient or somewhere within the machine to dissipate along a relatively high impedance fluid path, through the electrically floating fluid pathway and through an external used dialysate drain line, to the electrical earth at the house drain.

In light of the technical features set forth herein, and without limitation, in a first aspect, a renal failure therapy system includes: a dialyzer; a blood circuit in fluid communication with the dialyzer; a dialysis fluid circuit in fluid communication with the dialyzer; a housing supporting the dialyzer, the blood circuit and the dialysis fluid circuit; and at least one electrical socket held by the housing, the electrical socket providing a voltage output dedicated to a particular voltage type of external electrical device for powering or charging the external electrical device, the at least one electrical socket including electrical insulation for protecting a patient while powering the external electrical device.

In a second aspect, which may be used in combination with any other aspect described herein unless specified otherwise, the voltage output dedicated to a particular voltage type of external electrical device is a USB voltage output.

In a third aspect, which may be used in combination with any other aspect described herein unless specified otherwise, the voltage output dedicated to a particular voltage type of personal external device is a 5, 10 or 24 VDC output.

In a fourth aspect, which may be used in combination with any other aspect described herein unless specified otherwise, the voltage output dedicated to a particular voltage type of personal external device is a 120 or 240 VAC output.

In a fifth aspect, which may be used in combination with any other aspect described herein unless specified otherwise, the electrical insulation of the at least one electrical socket includes a transformer.

In a sixth aspect, which may be used in combination with any other aspect described herein unless specified otherwise, the electrical insulation of the at least one electrically insulated electrical socket includes a DC to DC converter.

In a seventh aspect, which may be used with the sixth aspect in combination with any other aspect described herein unless specified otherwise, the DC to DC converter includes an input conductively insulated from an output.

In an eighth aspect, which may be used in combination with any other aspect described herein unless specified otherwise, the electrical insulation of the at least one electrical socket includes a transformer in combination with (i) an AC to DC converter or (ii) a DC to AC converter and an AC to DC converter.

In a ninth aspect, which may be used in combination with any other aspect described herein unless specified otherwise, the renal failure therapy system includes a bank of electrical sockets providing a first voltage output dedicated to a same particular voltage type of the external electrical device.

In a tenth aspect, which may be used with the ninth aspect in combination with any other aspect described herein unless specified otherwise, the bank is a first bank, and which includes a second bank of electrical sockets providing a second voltage output dedicated to a same particular voltage type of second external electrical device, the second voltage different from the first voltage.

In an eleventh ninth aspect, which may be used in combination with any other aspect described herein unless specified otherwise, the renal failure therapy system includes an electrically floating fluid pathway provided in at least a portion of the blood circuit and at least a portion of the dialysis fluid circuit, wherein the only electrical path to ground is via used dialysis fluid traveling through the machine to electrical earth.

In a twelfth aspect, which may be used with the eleventh aspect in combination with any other aspect described herein unless specified otherwise, at least one electrically sensitive component in the at least portion of the dialysis fluid circuit of the electrically floating fluid pathway is electrically bypassed.

In a thirteenth aspect, which may be used with the twelfth in combination with any other aspect described herein unless specified otherwise, the at least one electrically sensitive component is electrically insulated from its power and signal input wires.

In a fourteenth aspect, which may be used with the eleventh aspect in combination with any other aspect described herein unless specified otherwise, the renal failure therapy system includes an external drain line and a drain having an electrical earth, and wherein the electrically floating fluid pathway leads to the external drain line, which leads to the drain.

In a fifteenth aspect, which may be used in combination with any other aspect described herein unless specified otherwise, a renal failure therapy machine for providing treatment to a patient using an external electrical device includes: a dialyzer; a blood circuit in fluid communication with the dialyzer; a dialysis fluid circuit in fluid communication with the dialyzer; a housing supporting the dialyzer, the blood circuit and the dialysis fluid circuit; and an electrical socket held by the housing, the electrical socket providing a voltage output dedicated to a voltage of the external electrical device for powering or charging the external electrical device, the electrical socket including electrical insulation for protecting a patient while powering the external electrical device.

In a sixteenth aspect, which may be used with the fifteenth aspect in combination with any other aspect described herein unless specified otherwise, there is no protective earth connection within or on the housing to any fluid flowing within the dialysis fluid circuit.

In a seventeenth aspect, which may be used with the fifteenth aspect in combination with any other aspect described herein unless specified otherwise, there is no protective earth connection within or on the housing to any fluid flowing within the blood circuit or dialyzer.

In an eighteenth aspect, which may be used with the fifteenth aspect in combination with any other aspect described herein unless specified otherwise, the electrical socket is a first socket and the voltage output is a first voltage output, and wherein the housing supports a second electrical socket providing a second voltage output different than the first voltage output.

In a nineteenth aspect, which may be used with any other aspect described herein unless specified otherwise, the electrical insulation is or includes double electrical insulation.

In a twentieth aspect, any of the features, functionality and alternatives described in connection with any one or more of FIGS. 1 to 7 may be combined with any of the features, functionality and alternatives described in connection with any of the other one or more of FIGS. 1 to 7.

It is therefore an advantage of the present disclosure to provide a hemodialysis, hemofiltration or hemodiafiltration system and method having electrically insulated electrical sockets.

It is another advantage of the present disclosure to provide a hemodialysis, hemofiltration or hemodiafiltration system and method having electrically insulated electrical sockets in combination with electrically insulated input lines to the socket to provide double insulated electrical sockets.

It is another advantage of the present disclosure to provide a hemodialysis, hemofiltration or hemodiafiltration system and method having electrical sockets that enable a patient to safely power and/or charge an external electrical device during treatment.

It is a further advantage of the present disclosure to provide a hemodialysis, hemofiltration or hemodiafiltration system and method having electrically insulated electrical sockets provided in combination with fluid lines that are additionally electrically insulated.

It is yet another advantage of the present disclosure to provide a hemodialysis, hemofiltration or hemodiafiltration system and method having electrically insulated electrical sockets provided in combination with fluid lines that are electrically floating within the blood tubing and the renal failure treatment machine.

It is yet a further advantage of the present disclosure to provide a hemodialysis, hemofiltration or hemodiafiltration system and method having electrical sockets that enable a patient to safely power and/or charge an external electrical device during treatment in combination with electrical insulation that mitigates the effects of fault voltages that may still be generated at the patient, in the blood lines, or in the dialysis fluid lines.

The advantages discussed herein may be found in one, or some, and perhaps not all of the embodiments disclosed herein. Additional features and advantages of the present invention are described in, and will be apparent from, the following Detailed Description of the Invention and the figures.

DETAILED DESCRIPTION

Figure 1:
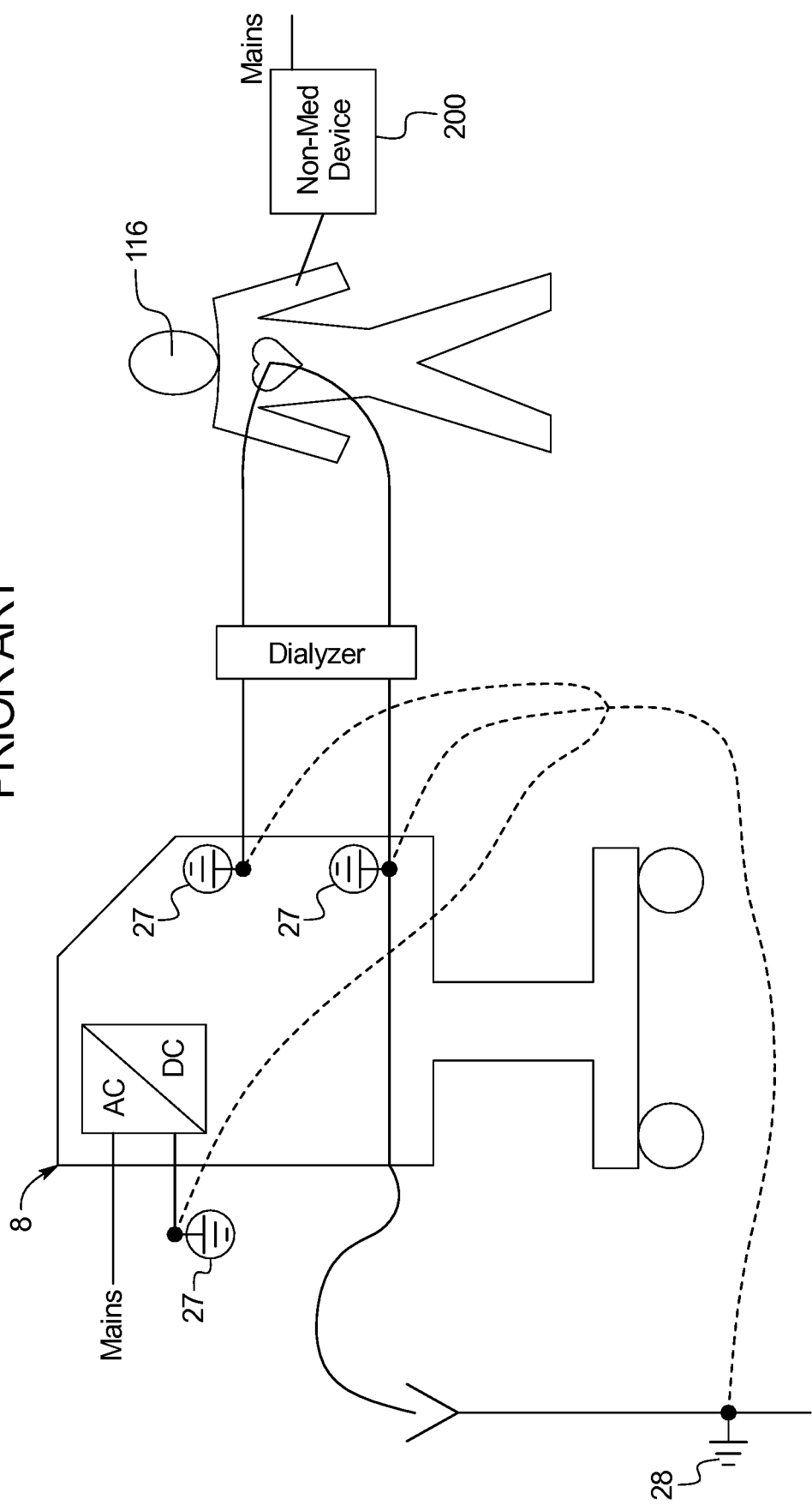
FIG. 1 illustrates one example of a potential electrical insulation problem with existing renal failure therapy machines.

Referring now to the drawings and in particular to FIG. 1, a known dialysis machine 8 connected to a patient 116 illustrates a potential electrical insulation problem. Known machine 8 is connected within its housing to machine protective earth 27 in multiple places to protect various components, such as conductivity sensors, which may read improperly when subjected to currents due to fault voltages. The system's protective earth connections take the fault currents instead to protective earth 27, protecting the sensing equipment. Machine 8 is also connected outside its housing to electrical earth 28.

Protective earth 27 for known machine 8 is also intended to ensure that the patient is safe from an internal electrical failure occurring within machine 8. However, an electrical risk to patient 116 is created because the patient is electrically connected via conductive dialysis fluid to protective earth 27. If patient 116 touches a faulty piece of electrical equipment having an electrical potential relative to protective earth, a potentially dangerous current may flow from the faulty equipment through patient 116, to protective earth 27.

Patient 116 in the illustrated embodiment is handling an external electrical device 200, which may be any type of electrical device, such as a reading lamp, heating pad, etc. In many cases, external electrical device 200 will be a personal communication/computing device ("PCD"), such as a smart phone, tablet, or personal computer. In any case, the external electrical device 200 is connected to mains power in FIG. 1.

Many PCD's are provided with cheaply made chargers, which are prone to failure. When the chargers fail, a very real potential for a fault voltage is created. When a fault voltage is created, if there is a path to electrical earth 28, a fault current will be generated. The system's connections to protective earth 27 within known machine 8, which provide low impedance paths to protect the sensing equipment, also provide a low impedance path for the fault current.

In many instances, needle access to patient 116 is into a vein in one of the patient's arms. FIG. 1 illustrates an alternative needle access established in which a central venous catheter ("CVC") is inserted into vein very close to the patient's heart. In this scenario, fault voltages, such as those just described, present a heightened risk due to the proximity to the patient's heart.

It is advisable for dialysis clinics to prevent the patient from powering an external electrical device 200 using the clinic's mains pour during treatment. It is difficult to ensure however that every clinic will follow this procedure for every treatment. Certain patients, perhaps not understanding the risk, may disobey the rules and plug their device 200 into the mains power system when left unattended. Moreover, chronic kidney failure treatments may last hours, leading to an ever-increasing desire for the patients to want to power their PCD's 200.

Figure 2:
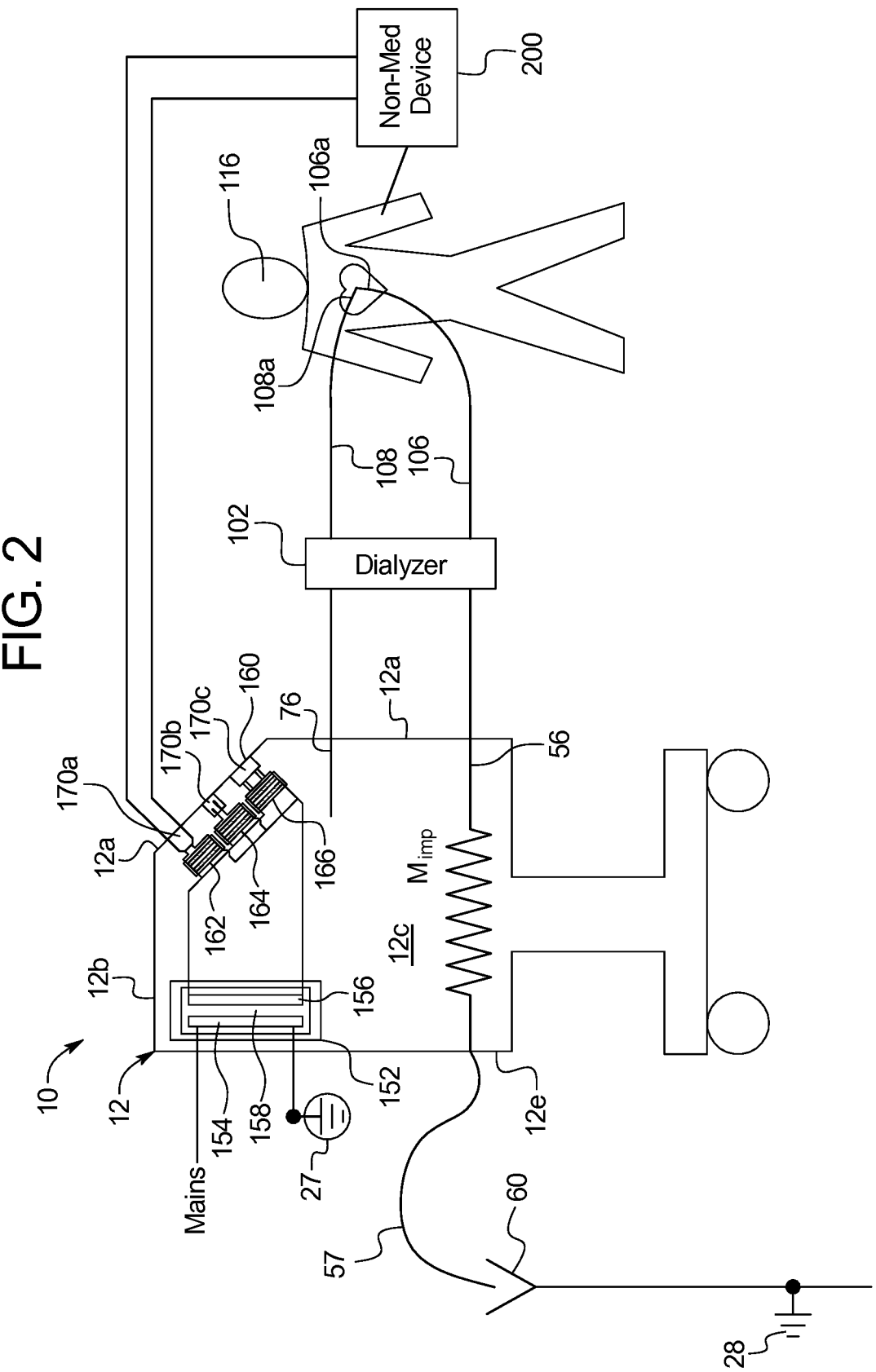
FIG. 2 is a side elevation view of one embodiment of an electrically insulated renal failure therapy machine of the present disclosure.

Referring now to FIG. 2, system 10 having renal failure therapy machine 12 provides a solution to the above described problem. Machine 12 provides a renal failure therapy to patient 116. The components of machine 12 are discussed in detail below. For now, it is enough to know that machine 12 may include internal components that prepare a dialysis fluid, and pump such dialysis fluid along a fresh dialysis fluid line 76 to a dialyzer 102. The internal components of machine 12 also pump used dialysis fluid from dialyzer 102 along a used dialysis fluid line 56 to an external drain line 57 and to drain 60.

Machine 12 also includes a blood pump that pumps blood from patient 116 along an arterial line 106 and pushes the blood through dialyzer 102 and venous line 108, back to patient 116. The blood pump 120, dialyzer 102, arterial line 106 and venous line 108 are typically located at the front 12*a* of machine 12. Machine front 12*a* is accordingly generally open and accessible to the nurse and patient and provides a convenient location 160 for one or more electrically insulated electrical socket 170. In alternative embodiments, insulated socket location 160 is provided on any one or more of machine top 12*b*, machine sides 12*c* and 12*d* (12*d* not viewable in FIG. 2), or machine backside 12*e*.

In the illustrated embodiment, location 160 includes differently rated insulated electrical sockets 170*a*, 170*b*, and 170*c* (referred to herein collectively as sockets 170 and generally, individually as socket 170). Sockets 170 may for example be dedicated to Universal Serial Bus ("USB") charging 170*a*, 12 VDC or 24 VDC charging 170*b*, or 120 VAC or 220 VAC charging 170*c*. Each socket 170*a*, 170*b*, and 170*c* is accordingly dedicated to a particular voltage type of external electrical device 200. The side section view of FIG. 2 is only able to show a single ("USB") socket 170*a*, a single 12 VDC or 24 VDC socket 170*b*, and a single 120 VAC or 220 VAC socket 170*c*. It should be appreciated that there may be a bank 162 of multiple ("USB") sockets 170*a*, a bank 164 of multiple 12 VDC or 24 VDC sockets 170*b*, and a bank 166 of 120 VAC or 220 VAC sockets 170*c*.

Figure 3A:
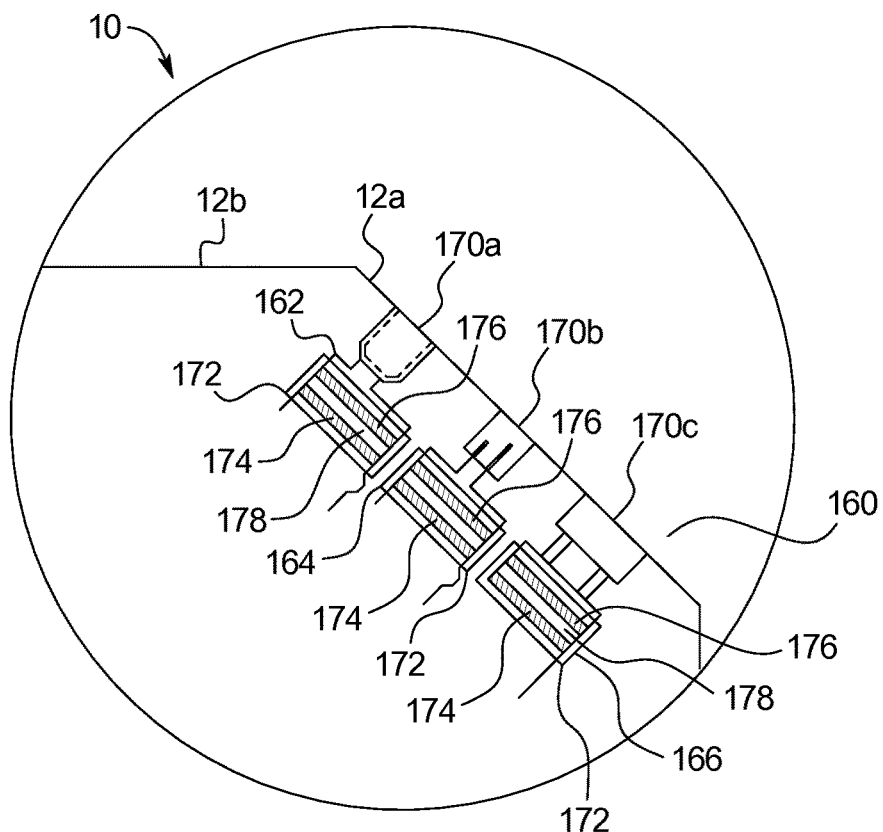
FIGS. 3A and 3B are exploded side and front elevation views, respectively, illustrating one example of the insulated electrical sockets of the present disclosure.

Referring now to FIG. 3A, an exploded view of the socket bank location 160 of FIG. 2 is illustrated. For ease of illustration, each of USB sockets 170*a*, 12 VDC or 24 VDC sockets 170*b*, and 120 VAC or 220 VAC sockets 170*c* is illustrated as having a transformer 172 having a primary coil 174 and a secondary coil 176. Each primary coil 174 is separated from a secondary coil 176 by an isolation barrier 178, which may be air gap or gap filled with electrically resistive potting material. Isolation barrier 178 provides a conductive break, which conductively isolates components "downstream" from secondary coil 176, including patient 116, from any electrically connected component upstream of primary coil 174, including mains voltage illustrated in FIG. 2. Primary coil 174 and secondary coil 176 are magnetically coupled, such that primary coil 174 induces a desired AC voltage in secondary coil 176.

Primary coil 174 and secondary coil 176 of transformer 172 is one preferred way of isolating 120 VAC or 220 VAC sockets 170*c* and for providing the desired AC voltage for the power sockets. Patient 116 may use 120 VAC or 220 VAC sockets 170*c* for example to power a personal computer 200 using the patient's existing computer power cord. Computer power cords typically provide their own transformers, which output a desired voltage to the computer 200. The transformers may provide their own electrical insulation, which in certain instances is unreliable. 120 VAC or 220 VAC sockets 170*c* provide reliable electrical insulation, which protects the patient even if the insulation of the computer cord transformer is faulty.

DC sockets 170*a* and 170*b* and their corresponding electrical isolation may be provided in a variety of different ways. In one embodiment the input DC voltage is converted to an input AC voltage using a DC to AC converter (illustrated in FIG. 5). The input AC voltage is conductively isolated from an AC output voltage via a transformer 172 and its isolation barrier 178 as illustrated in FIG. 3A, wherein primary coil 174 induces a desired AC output voltage in secondary coil 176. An AC to DC converter (illustrated in FIG. 5) is provided on the output side of transformer 172 to convert the induced AC output voltage to a desired DC output, e.g., 5 VDC, 12 VDC or 24 VDC.

Figure 3B:
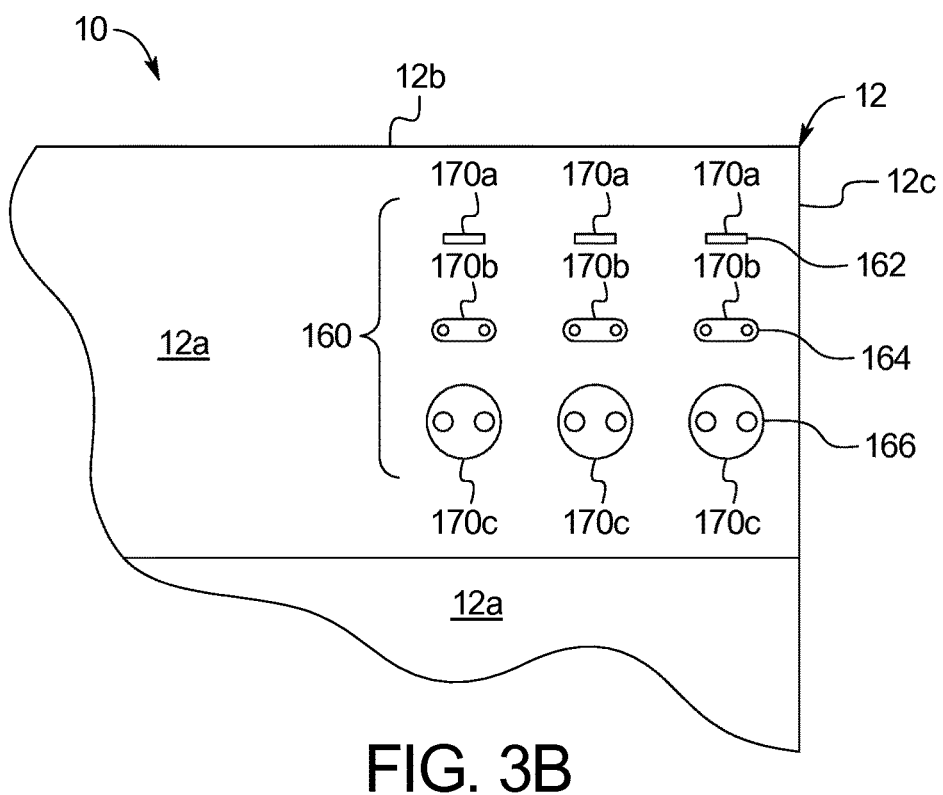

FIG. 3B shows a front view of FIG. 3A, better illustrating banks 162, 164, and 166 of electrically insulated sockets 170*a* to 170*c*. As illustrated, for example, there may be nine total sockets, with a bank 162 of three USB sockets 170*a*, a bank 164 of multiple 12 VDC or 24 VDC sockets 170*b*, and a bank 166 of 120 VAC or 220 VAC sockets 170*c*. Or perhaps there are multiple USB sockets 170*a*, multiple 12 VDC or 24 VDC sockets 170*b*, but only a single 120 VAC or 220 VAC socket. The combination of sockets may be chosen as desired to meet the most likely demand.

Figure 4:
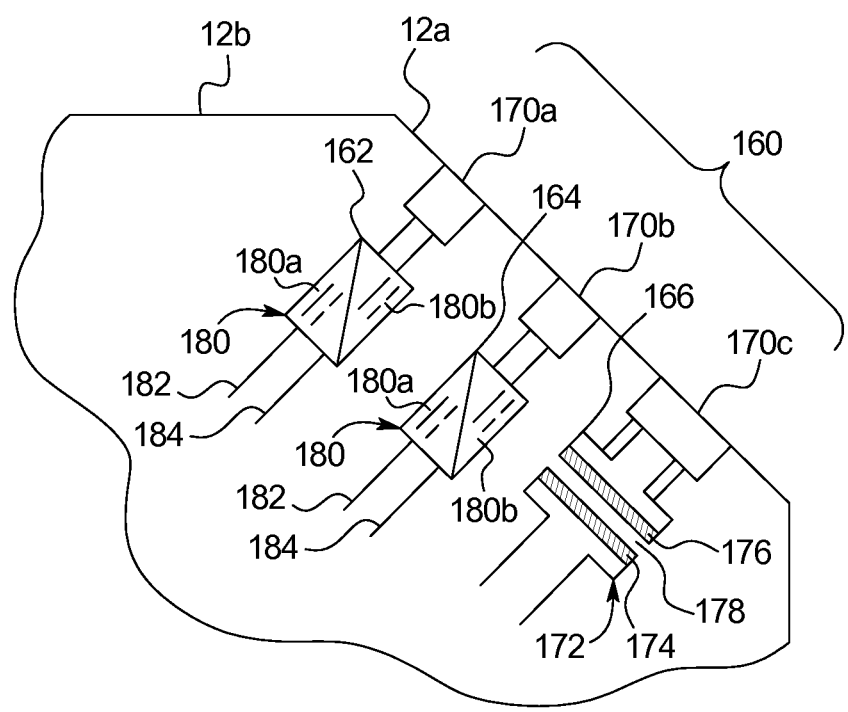
FIG. 4 is a side exploded view illustrating another example of the insulated electrical sockets of the present disclosure.

Referring now to FIG. 4, an alternative embodiment for providing DC sockets 170a and 170b is illustrated. Here, a DC to DC converter 180 receives system DC power, e.g., 24 VDC, via system power and power ground wires 182 and 184, respectively. An input 180a of DC to DC converter 180 receives DC input power (e.g., 24 VDC) from system power and power ground wires 182 and 184. Input 180a charges output 180b while being conductively isolated from output 180b. DC to DC converter 180 may perform the isolated charging in different ways as discussed below.

In any of the embodiments discussed above, transformer 172 may include a dedicated primary coil 174 for each output coil 176. Alternatively, there may be a single primary coil 174 for multiple output coils 176, where the output coils 176 may be of the same or different output voltage (e.g., different output coils may have different winding sizes and/or turns ratios to produce a different output voltage). For DC to DC conversion, a DC input voltage may be converted to an AC input voltage using a DC to AC converter, where the AC input voltage powers a common coil for multiple output coils, which each produce an AC output voltage. To this end, transformer 172 can have multiple windings or windings with several connection points (taps) on both the primary and secondary or output sides of transformer 172. An AC to DC converter may also be provided for each AC output voltage to produce multiple DC output voltages each having a desired DC output level. For desired DC outputs, it is also contemplated to begin with an AC input voltage, induce an AC output voltage on output coil 176, and convert the AC output voltage to a desired one or more DC output voltage.

Figure 5:
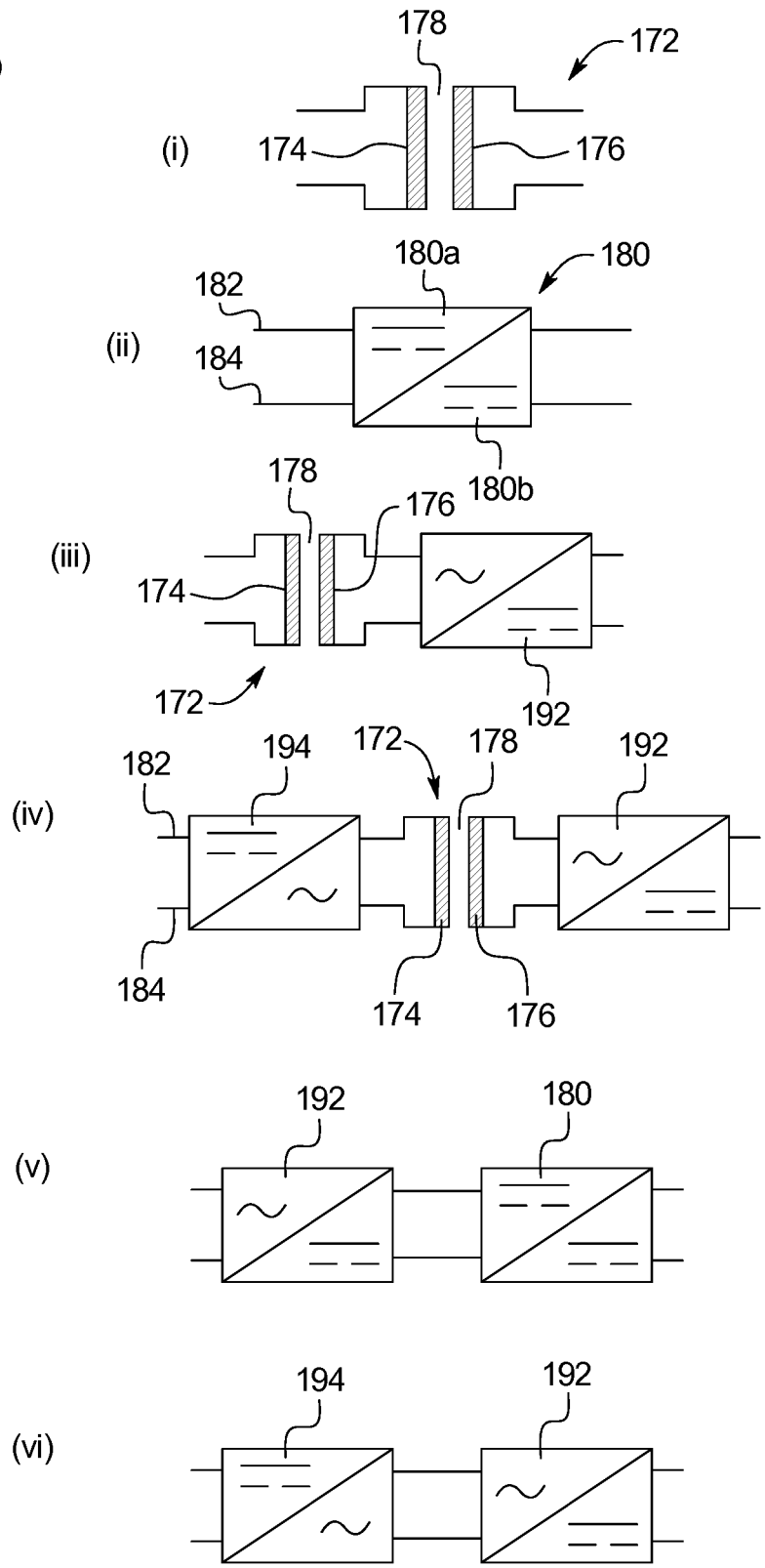
FIG. 5 is a schematic view illustrating various types of electrical conversion and isolation suitable for use with the insulated electrical sockets of the present disclosure.

FIG. 5 summarizes that machine 12 of system 10 may provide electrical insulation for any combination of electrically insulated sockets 170a to 170c via any combination of (i) straight AC to AC transformers 172, (ii) straight DC to DC converters 180, (iii) AC to AC transformers 172 in combination with AC to DC conversion 192, (iv) AC to AC transformers 172 in combination with DC to AC conversion 194 and AC to DC conversion 192, (v) AC to DC conversion 192 in combination with DC to DC conversion 180, and (vi) DC to AC conversion 194 in combination with AC to DC conversion 192 without a transformer 172. Other options providing galvanic separation for the patient include capacitive coupling for AC power, Hall effect sensors, and optical devices for DC power.

FIGS. 3A, 3B and 4 show in detail a first layer of electrical insulation between patient 116 and mains power provided by electrically insulated sockets 170a, 170b and 170c. FIG. 2 illustrates a second layer of electrical insulation between patient 116 and mains power, namely, a mains transformer 152 having a mains input coil 154 and a mains output coil 156 separated by an isolation barrier 158. Mains transformer 152 is located between mains power and the input or inputs to electrically insulated sockets 170a, 170b and 170c. Isolation barrier 158 prevents the conducting of electricity, while input coil 154 induces a desired voltage in output coil 156, as has been described above.

FIG. 2 illustrates that output coil 156 of mains transformer 152 powers the input sides of each of the transformers of electrically insulated sockets 170a, 170b and 170c. This may occur if, for example, the output AC voltages at output coils 176 of the transformers 172 of DC sockets 170b and 170c are converted within the sockets using AC to DC converters 152 (FIG. 5) to the desired DC voltages. Alternatively, output coil 156 of mains transformer 152 is split into an AC power circuit and one or more DC power circuit (not illustrated) using one or more AC to DC converter. Here, the output of the AC power circuit powers the inputs of electrically insulated AC socket 170a, while the one or more DC power circuit powers the inputs of electrically insulated DC sockets 170b and 170c, e.g., using isolated DC to DC.

FIG. 2 illustrates the double electrical insulation between external electrical device 200 and mains power as has just been described. Again, the double insulation helps to prevent the patient from being subjected to stray or fault voltages due for example to a faulty external electrical device 200. FIG. 2 also illustrates that system 10 provides additional electrical insulation, which helps to mitigate the effects of a stray or fault voltage that does occur due for example to a faulty external electrical device 200. As illustrated in FIG. 2, machine impedance $M_{imp}$ is made to be as large as possible so as to reduce the current resulting from a fault or stray voltage as much as possible. To do so, no connection is made between (ai) the blood in blood set, (aii) the dialysis fluid in fresh or used dialysis fluid lines, (aiii) the concentrates in concentrate lines, and (aiv) water in water lines (which may not be properly deionized, each of (ai) to (aiv) is considered to be at least somewhat conductive) and (b) machine or electrical earth 28. As illustrated in FIG. 1, prior art machines are typically connected to protective earth 27 at multiple places, for example, in the used dialysis line just downstream of the dialyzer. Configured as described above, there is no physical connection to electrical earth 28 within the fluid pathways of system 10, such that the pathways within the machine are said to be electrically floating, causing any fault or stray currents to flow through the increased machine impedance $M_{imp}$ and through an external drain line 57 to electrical earth 28 at drain 60 located outside of machine 12, thereby reducing the fault or stray current.

Figure 6:
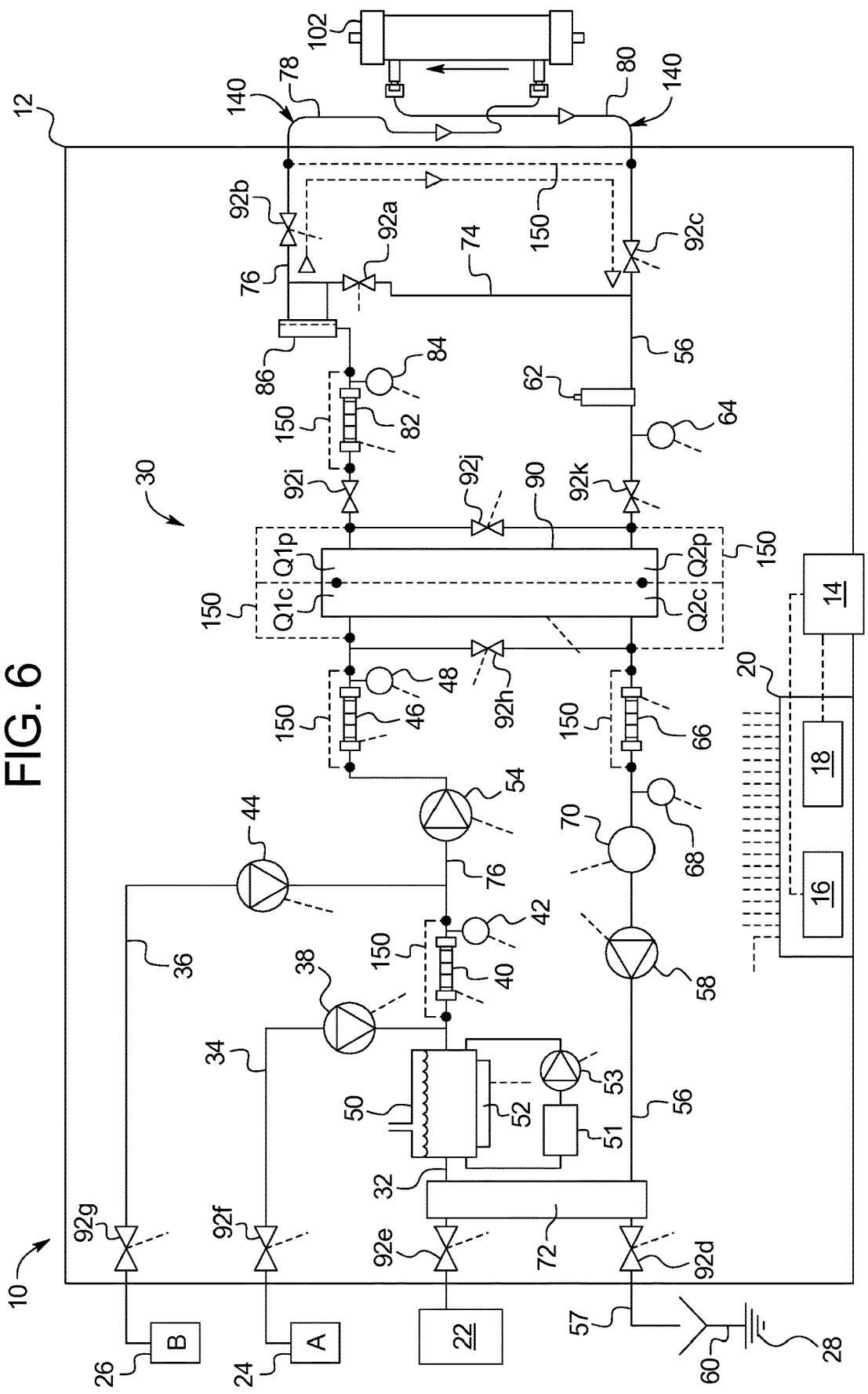
FIG. 6 illustrates one embodiment of a dialysis fluid circuit forming part of an electrically floating fluid pathway, which may be used with the insulated electrical sockets of the present disclosure.
Figure 7:
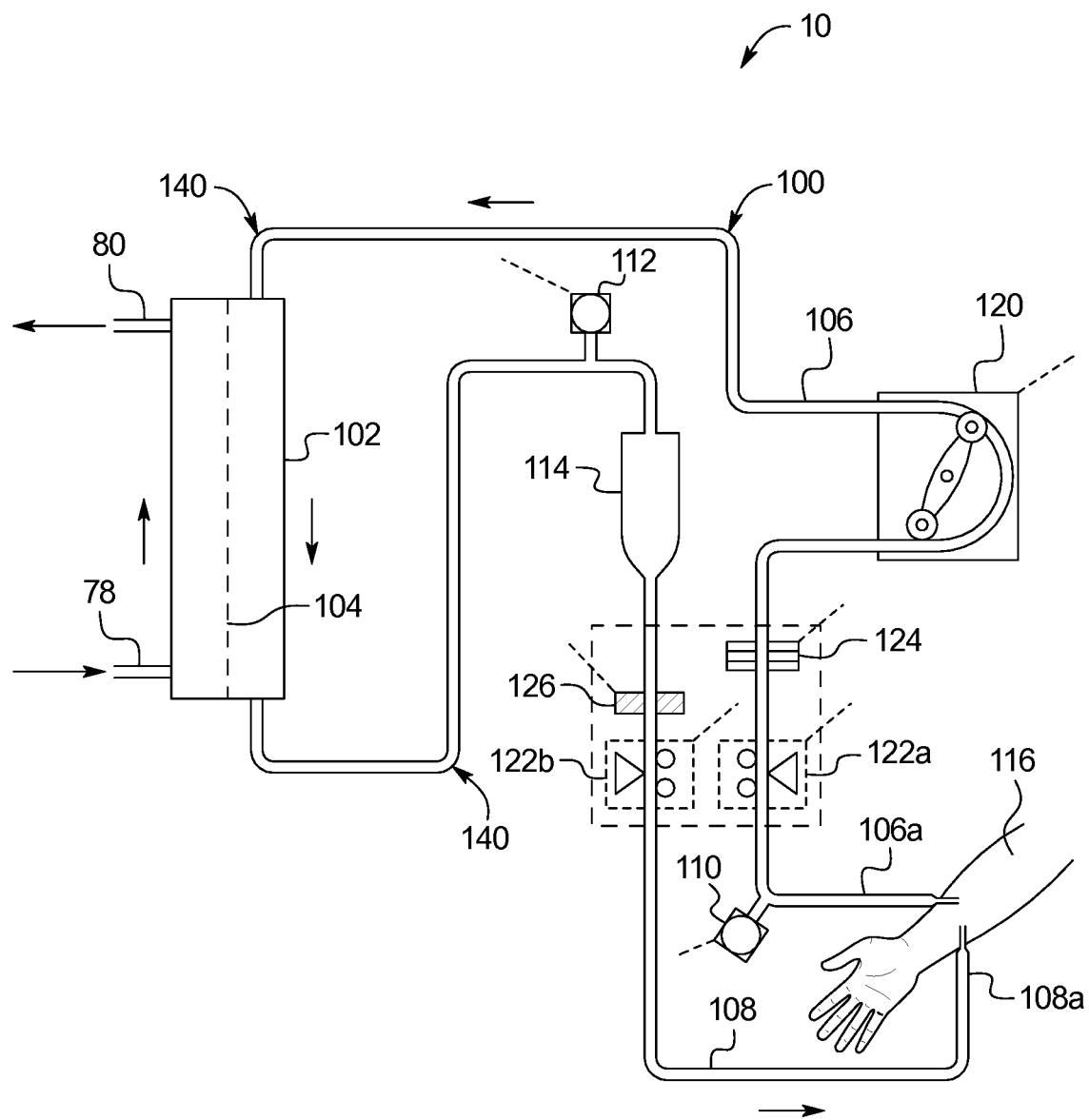
FIG. 7 illustrates one embodiment of a blood fluid circuit forming part of an electrically floating fluid pathway, which may be used with the insulated electrical sockets of the present disclosure.

FIGS. 6 and 7 illustrate an embodiment of an electrically floating fluid pathway 140 of system 10. System 10 in FIG. 6 includes a machine 12 having an enclosure or housing. The housing may provide the insulated electrical socket 170 and described above. The housing of machine 12 holds the contents of a dialysis fluid or dialysis fluid circuit 30 described in detail below. The housing or machine 12 also supports a user interface 14, which allows a nurse or other operator to interact with system 10. User interface 14 may have a monitor screen operable with a touch screen overlay, electromechanical buttons, e.g., membrane switches, or a combination of both. User interface 14 is in electrical communication with at least one processor 16 and at least one memory 18. At least one processor 16 and at least one memory 18 also electronically interact with, and where appropriate, control the pumps, valves and sensors described herein, e.g., those of dialysate circuit 30. At least one processor 16 and at least one memory 18 are referred to collectively herein as a logic implementer 20. The dashed lines extending from logic implementer 20 lead to pumps, valves, sensors, the heater and other electrical equipment, as indicated by like dashed lines leading from the pumps, valves, sensors, heater, etc.

Dialysis fluid circuit 30 includes a purified water line 32, an A-concentrate line 34 and a bicarbonate B-concentrate line 36. Purified water line 32 receives purified water from a purified water device or source 22. The water may be purified using any one or more process, such as, reverse osmosis, carbon filtering, ultraviolet radiation, electrodeionization ("EDI"), and/or ultrafiltering.

An A-concentrate pump 38, such as a peristaltic or piston pump, pumps A-concentrate from an A-concentrate source 24 into purified water line 32 via A-concentrate line 34.

Conductivity cell 40 measures the conductive effect of the A-concentrate on the purified water, sends a signal to logic implementer 20, which uses the signal to properly proportion the A-concentrate by controlling A-concentrate pump 38. The A-conductivity signal is temperature compensated via a reading from temperature sensor 42.

A B-concentrate pump 44, such as a peristaltic or piston pump, pumps B-concentrate from a B-concentrate source 26 into purified water line 32 via B-concentrate line 36. Conductivity cell 46 measures the conductive effect of the B-concentrate on the purified water/A-concentrate mixture, sends a signal to logic implementer 20, which uses the signal to properly proportion the B-concentrate by controlling B-concentrate pump 44. The B-conductivity signal is also temperature compensated via a reading from temperature sensor 48.

A water tank 50 holds purified water prior to receiving the concentrates, which has been degassed in a degassing chamber 51 via a degassing pump 53, located below water tank 50. A heater 52 controlled by logic implementer 20 heats the purified water for treatment to body temperature, e.g., 37° C. The fluid exiting conductivity cell 46 is therefore freshly prepared dialysis fluid, properly degassed and heated, and suitable for sending to dialyzer 102 for treatment. A fresh dialysis fluid pump 54, such as a gear pump, delivers the fresh dialysis fluid to dialyzer 102. Logic implementer 20 controls fresh dialysis fluid pump 54 to deliver fresh dialysis fluid to the dialyzer at a specified flowrate as described in more detail below.

A used dialysis fluid line 56 via a used dialysis fluid pump 58 returns used dialysis fluid from the dialyzer through an external drain line 57 to a drain 60. Logic implementer 20 controls used dialysis fluid pump 58 to pull used dialysis fluid from dialyzer 102 at a specified flowrate. An air separator 62 separates air from the used dialysis fluid in used dialysis fluid line 56. A pressure sensor 64 senses the pressure of used dialysis fluid within used dialysis fluid line 56 and sends a corresponding pressure signal to logic implementer 20.

Conductivity cell 66 measures the conductivity of used fluid flowing through used dialysis fluid line 56 and sends a signal to logic implementer 20. The conductivity signal of cell 66 is also temperature compensated via a reading from temperature sensor 68. A blood leak detector 70, such as an optical detector, looks for the presence of blood in used dialysis fluid line 56, e.g., to detect if a dialyzer membrane has a tear or leak. A heat exchanger 72 recoups heat from the used dialysis fluid exiting dialysis fluid circuit 30 to drain 60, preheating the purified water traveling towards heater 52 to conserve energy.

A fluid bypass line 74 allows fresh dialysis fluid to flow from fresh dialysis fluid line 76 to used dialysis fluid line 56 without contacting dialyzer 102. A fresh dialysis fluid tube 78 extends from machine 12 and carries fresh dialysis fluid from fresh dialysis fluid line 76 to dialyzer 102. A used dialysis fluid tube 80 also extends from machine 12 and carries used dialysis fluid from dialyzer 102 to used dialysis fluid line 56.

Fresh dialysis fluid line 76 also includes a conductivity sensor or cell 82 that senses the conductivity of fresh dialysis fluid leaving a UF system 90 and sends a corresponding signal to logic implementer 20. The conductivity signal of cell 82 is likewise temperature compensated via a reading from temperature sensor 84.

An ultrafilter 86 further purifies the fresh dialysis fluid before being delivered via dialysis fluid line 76 and fresh dialysis fluid tube 78 to dialyzer 102. Alternatively or additionally, one or more ultrafilter (additional ultrafilter is not illustrated) is used to purify the fresh dialysis fluid to the point where it may be used as substitution to perform from pre- or post-dilution hemofiltration or hemodiafiltration.

UF system 90 monitors the flowrate of fresh dialysis fluid flowing to dialyzer 102 (and/or as substitution fluid flowing directly to the blood set (FIG. 2)) and used fluid flowing from the dialyzer. UF system 90 includes fresh and used flow sensors Q1c and Q2c, respectively, which send signals to logic implementer 20 indicative of the fresh and used dialysis fluid flowrate, respectively. Logic implementer 20 uses the signals to set used dialysis fluid pump 58 to pump faster than fresh dialysis fluid pump 54 by a predetermined amount to remove a prescribed amount of ultrafiltration ("UF") from the patient over the course of treatment. Fresh and used flow sensors Q1p and Q2p are redundant sensors that ensure UF system 90 is functioning properly.

System 10 provides plural valves 92 (referring collectively to valves 92a to 92k) under the control of logic implementer 20 to selectively control a prescribed treatment. In particular, valve 92a selectively opens and closes bypass line 68, e.g., to allow disinfection fluid to flow from fresh dialysis fluid line 76 to used dialysis fluid line 56. Valve 92b selectively opens and closes fresh dialysis fluid line 76. Valve 92c selectively opens and closes used dialysis fluid line 56. Valve 92d selectively opens and used dialysis fluid line 56 to external drain line 57 and drain 60. Valve 92e selectively opens and closes purified water line 32 to purified water source 22. Valves 92f and 92g control A- and B-concentrate flow, respectively. Valves 92h to 92k operate with UF system 90.

It should be appreciated that the dialysis fluid circuit 30 is simplified and may include other structure (e.g., more valves) and functionality not illustrated. Also, dialysis fluid circuit illustrates a hemodialysis ("HD") pathway. It is contemplated to provide an additional ultrafilter (not illustrated) in fresh dialysis fluid line 76 to create substitution fluid for hemofiltration ("HF"). It is also contemplated to provide one or more ultrafilter in one or more line(s) branching off of fresh dialysis fluid line 76 to create substitution fluid, in addition to the fresh dialysis fluid in line 76, for hemodiafiltration ("HDF").

Referring now to FIG. 7, blood circuit or set 100 illustrates one embodiment of a blood set that may be used with either system 10. Blood circuit or set 100 includes a dialyzer 102 having many hollow fiber semi-permeable membranes 104, which separate dialyzer 102 into a blood compartment and a dialysis fluid compartment. The dialysis fluid compartment during treatment is placed in fluid communication with a distal end of fresh dialysis fluid tube 78 and a distal end of used dialysis fluid tube 80. For HF and HDF, a separate substitution tube, in addition to fresh dialysis fluid tube 78, is placed during treatment in fluid communication with one or both of arterial line 106 extending from an arterial access 106a and venous line 108 extending to a venous access 108a. In HDF, dialysis fluid also flows through dialysis fluid tube 78 to dialyzer 102, while for HF, dialysis fluid flow through tube 78 is blocked.

An arterial pressure pod 110 may be placed upstream of blood pump 120, while venous line 108 includes a venous pressure pod 112. Pressure pods 110 and 112 operate with blood pressure sensors (not illustrated) mounted on the machine housing, which send arterial and venous pressure signals, respectively, to logic implementer 20. Venous line 108 includes a venous drip chamber 114, which removes air from the patient's blood before the blood is returned to patient 116.

Arterial line 106 of blood circuit or set 100 is operated by blood pump 120, which is under the control of logic implementer 20 to pump blood at a desired flowrate. System 10 also provides multiple blood side electronic devices that send signals to and/or receive commands from logic implementer 20. For example, logic implementer 20 commands pinch clamps 122a and 122b to selectively open or close arterial line 106 and venous line 108, respectively. A blood volume sensor ("BVS") 124 is located along arterial line 106 upstream of blood pump 120. Air detector 126 looks for air in venous blood line 108.

To create the electrically floating dialysis fluid circuit 30, sensitive equipment, such as conductivity sensors 40, 46, 66 and 82, which are normally connected directly or indirectly to protective earth 27, are instead left floating with respect to protective earth 27 or other earth within machine 12. Likewise, the flow sensors Q1c, Q2c, Q1p, and Q2p of UF system 90 are not connected to protective earth. In the illustrated embodiment, nowhere within machine 12 is electrically floating dialysis fluid circuit 30 or the floating blood set 100 physically connected to protective earth 27 or other electrical earth. Thus, dialysis fluid circuit 30 and the blood set 100 (including arterial line 106, venous line 108, and patient access or needles 106a, 108a) with respect to machine 12 are said to be electrically floating.

The sensitive equipment, however, is in the prior art connected to protective earth 27 for a reason, namely, if not properly earthed, stray current from outside or inside the machine or a faulty component may cause the conductivity and flow sensors to read or output improperly. To combat this problem without connecting the sensors to protective earth 27, the sensors of the present disclosure are provided with electrical bypass lines 150 as illustrated in FIG. 6. Bypass lines 150 electrically bypass the sensing equipment, from a point upstream of the sensors to a point downstream of the sensors, so that fault currents conduct from upstream to downstream of each sensor, or vice versa, through electrical bypasses 150 and not the sensing equipment. In doing so, bypass lines 150 electrically contact, or are otherwise in electrical communication with, fluid upstream of the sensors and fluid downstream of the sensors, creating a short circuit around the sensors. The short circuit causes stray currents to bypass the sensors, so that the stray currents do not affect the operation of the sensors.

Additionally, the sensors and any other flow component conductively touching liquid in the dialysis fluid circuit 30 and the blood set 100 is electrically insulated from the remainder of machine 12 via mechanical insulation. Mechanical insulation refers to the use of a non-conductive material, e.g., plastic, rubber, ceramic, and combinations thereof, placed between the fluid contacting component and the machine. The result may be an insulating pad located between the component and the machine chassis or other machine fixture to which the component is mounted.

Besides, the "mechanical" electrical insulation, to make the dialysis fluid circuit 30 and the blood set 100 floating, electrical power wires and electrical signal wires that conduct signals away from the sensor probes or other structures that contact the blood, dialysis fluid or concentrate, for example, need to be electrically isolated from the circuitry and computational devices that read and analyze the sensor signals, e.g., printed circuit boards, processing, memory (discussed above as logic implementer 20). To do so, each power and signal wire stemming from a sensor is in one embodiment isolated via a transformer (or any of the described above for electrically insulated sockets 170a to 170c) from a power or signal wire, respectively, that extends from the transformer or other electrically insulating device to logic implementer 20 or power source. The transformers or other electrically insulating devices pass along the information carried by the sensor signal wiring, while creating a physical break in the signal lines. The physical breaks prevent (i) stray currents from machine 12 from entering the electrically floating fluid pathway 140 via the sensor power or signal lines and (ii) stray currents within floating fluid pathway 140 from exiting out to machine 12 and its other components via the sensor power or signal lines.

So to make the dialysis fluid circuit 30 and the blood set 100 electrically floating within machine 12, four features may be ensured: (i) no connection from a conductive fluid path to protective earth 27 or other electrical earth is made within machine 12 or in the blood set 100, (ii) sensitive equipment that touches conductive water, concentrate, dialysis fluid and/or blood in dialysis fluid circuit 30 and blood in blood set 100 is electrically bypassed, (iii) components that contact liquid are "mechanically" electrically insulated when mounted, and (iv) signal wires to or from logic implementer 20 are electrically isolated.

The above-described combination of different electrical insulation provides a significantly safer renal failure therapy system 10 versus known systems. It should be appreciated that the insulated electrical sockets of the present disclosure do not have to be used with the electrically floating fluid pathway 140, and vice versa, and that each make system 10 safer even if used alone. The present disclosure therefore does not require such combination.

ELEMENT NUMBER LISTING known dialysis machine 8
renal failure therapy system 10
renal failure therapy machine 12
user interface 14,
at least one processor 16,
at least one memory 18,
logic implementer 20,
purified water device or source 22,
A-concentrate source 24,
B-concentrate source 26,
machine protective earth 27,
electrical earth 28,
dialysis fluid circuit 30,
purified water line 32,
A-concentrate line 34,
B-concentrate line 36,
A-concentrate pump 38,
conductivity cell 40,
temperature sensor 42,
B-concentrate pump 44,
conductivity cell 46,
temperature sensor 48,
water tank 50,
degassing chamber 51,
dialysis fluid heater 52,
degassing pump 53,
fresh dialysis fluid pump 54,
used dialysis fluid line 56,
external drain line 57,
used dialysis fluid pump 58,
drain 60,
air separator 62,
pressure sensor 64,
dialyzer 102,
conductivity cell 66, temperature sensor 68,
blood leak detector 70,
heat exchanger 72,
fluid bypass line 74,
fresh dialysis fluid line 76,
fresh dialysis fluid tube 78,
used dialysis fluid tube 80,
conductivity cell 82,
temperature sensor 84,
ultrafilter 86,
UF system 90,
plural valves 92 (collectively to valves 92a to 92k),
blood circuit or set 100,
dialyzer 102,
semi-permeable membranes 104,
arterial line 106,
arterial access or needle 106a,
venous line 108,
venous access or needle 108a,
arterial pressure pod 110,
venous pressure pod 112,
venous drip chamber 114,
patient 116,
blood pump 120,
pinch clamps 122a and 122b,
blood volume sensor ("BVS") 124,
air detector 126,
floating fluid pathway 140,
electrical bypass lines 150,
mains transformer 152,
mains input coil 154,
mains output coil 156,
isolation barrier 158,
location 160 for electrically insulated sockets 170,
banks 162, 164, and 166 of electrically insulated sockets 170,
electrically insulated electrical sockets 170 (collectively to sockets 170a to 170c),
AC to AC transformer 172,
primary coil 174,
secondary coil 176,
isolation barrier 178,
DC to DC converter 180 having input 180a and output 180b,
power wire 182,
power ground wires 184,
AC to DC conversion 192,
DC to AC conversion 194
external electrical device 200

It should be understood that various changes and modifications to the presently preferred embodiments described herein will be apparent to those skilled in the art. Such changes and modifications may be made without departing from the spirit and scope of the present invention and without diminishing its intended advantages. It is therefore intended that such changes and modifications be covered by the appended claims.

The invention is claimed as follows:

1. A renal failure therapy system comprising:
a dialyzer;
a blood circuit in fluid communication with the dialyzer;
a dialysis fluid circuit in fluid communication with the dialyzer;
a housing supporting the dialyzer, the blood circuit and the dialysis fluid circuit; and
at least one electrical socket held by the housing, the electrical socket providing a voltage output dedicated to a voltage of an external electrical device for powering or charging the external electrical device, the at least one electrical socket including electrical insulation for protecting a patient while powering the external electrical device,
wherein an electrically floating fluid pathway is provided in at least a portion of the blood circuit and at least a portion of the dialysis fluid circuit, and wherein the only electrical path to ground is via used dialysis fluid traveling through the dialysis fluid circuit to electrical earth.

2. The renal failure therapy system of claim 1, wherein the voltage output is a Universal Serial Bus ("USB") voltage output.

3. The renal failure therapy system of claim 1, wherein the voltage output is selected from the group consisting of a 5 VDC output, a 10 VDC output, and a 24 VDC output.

4. The renal failure therapy system of claim 1, wherein the voltage output is selected from the group consisting of a 120 VAC output and a 240 VAC output.

5. The renal failure therapy system of claim 1, wherein the electrical insulation of the at least one electrical socket includes a transformer.

6. The renal failure therapy system of claim 1, wherein the electrical insulation of the at least one electrically insulated electrical socket includes a DC to DC converter.

7. The renal failure therapy system of claim 6, wherein the DC to DC converter includes an input conductively insulated from an output.

8. The renal failure therapy system of claim 1, wherein the electrical insulation of the at least one electrical socket includes a transformer in combination with (i) an AC to DC converter or (ii) a DC to AC converter and an AC to DC converter.

9. The renal failure therapy system of claim 1, which includes a bank of electrical sockets providing a first voltage output dedicated to the voltage of the external electrical device.

10. The renal failure therapy system of claim 9, wherein the bank is a first bank, and the renal failure therapy system includes a second bank of electrical sockets providing a second voltage output dedicated to a voltage of a second external electrical device, the second voltage output being different from the first voltage output.

11. The renal failure therapy system of claim 1, wherein at least one electrically sensitive component in the at least a portion of the dialysis fluid circuit of the electrically floating fluid pathway is electrically bypassed.

12. The renal failure therapy system of claim 11, wherein the at least one electrically sensitive component is electrically insulated from power and signal input wires of the at least one electrically sensitive component.

13. The renal failure therapy system of claim 1, which includes an external drain line and a drain having an electrical earth, and wherein the electrically floating fluid pathway leads to the external drain line, which leads to the drain.

14. The renal failure therapy system of claim 1, wherein the electrical insulation includes double electrical insulation.

15. A renal failure therapy machine for providing treatment to a patient using an external electrical device, the machine comprising:
a dialyzer;
a blood circuit in fluid communication with the dialyzer;
a dialysis fluid circuit in fluid communication with the dialyzer;
a housing supporting the dialyzer, the blood circuit and the dialysis fluid circuit; and an electrical socket held by the housing, the electrical socket providing a voltage output dedicated to a voltage of the external electrical device for powering or charging the external electrical device, the electrical socket including electrical insulation for protecting a patient while powering the external electrical device, wherein an electrically floating fluid pathway is provided in at least a portion of the blood circuit and at least a portion of the dialysis fluid circuit, and wherein the only electrical path to ground is via used dialysis fluid traveling through the dialysis fluid circuit to electrical earth.

16. The renal failure therapy machine of claim 15, wherein there is no protective earth connection within or on the housing to any fluid flowing within the dialysis fluid circuit.

17. The renal failure therapy machine of claim 15, wherein there is no protective earth connection within or on the housing to any fluid flowing within the blood circuit or dialyzer.

18. The renal failure therapy machine of any of claim 15, wherein the electrical socket is a first socket and the voltage output is a first voltage output, and wherein the housing supports a second electrical socket providing a second voltage output different than the first voltage output.

19. The renal failure therapy system of claim 15, wherein the electrical insulation includes double electrical insulation.

\* \* \* \* \*